United States Patent
Blouin et al.

(10) Patent No.: US 6,543,288 B1
(45) Date of Patent: Apr. 8, 2003

(54) LASER-ULTRASONIC MEASUREMENT OF ELASTIC PROPERTIES OF A THIN SHEET AND OF TENSION APPLIED THEREON

(75) Inventors: Alain Blouin, Montreal (CA); Benoit Reid, Montreal (CA); Jean-Pierre Monchalin, Montreal (CA)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 09/830,710

(22) PCT Filed: Nov. 3, 1999

(86) PCT No.: PCT/CA99/01025
§ 371 (c)(1),
(2), (4) Date: Aug. 6, 2001

(87) PCT Pub. No.: WO00/26628
PCT Pub. Date: May 11, 2000

Related U.S. Application Data

(60) Provisional application No. 60/107,069, filed on Nov. 4, 1998.

(51) Int. Cl.[7] .......................... G01N 29/08; G01N 29/24
(52) U.S. Cl. .............................. 73/643; 73/655; 73/657; 73/159
(58) Field of Search .................... 73/643, 645, 646, 73/655, 657, 159

(56) References Cited

U.S. PATENT DOCUMENTS

| | | | | |
|---|---|---|---|---|
| 4,622,853 A | * | 11/1986 | Leugers | 73/597 |
| 4,833,928 A | * | 5/1989 | Luukkala et al. | 73/862.391 |
| 4,966,459 A | | 10/1990 | Monchalin | 356/358 |
| 5,025,665 A | | 6/1991 | Keyes et al. | 73/597 |
| 5,035,144 A | * | 7/1991 | Aussel | 73/602 |
| 5,103,676 A | * | 4/1992 | Garcia et al. | 73/597 |
| 5,251,486 A | * | 10/1993 | Thompson et al. | 73/597 |
| 5,608,166 A | | 3/1997 | Monchalin et al. | 73/657 |
| 5,804,727 A | * | 9/1998 | Lu et al. | 73/597 |
| 5,814,730 A | | 9/1998 | Brodeur et al. | 73/597 |
| 6,356,846 B1 | * | 3/2002 | Haberger et al. | 702/40 |

* cited by examiner

Primary Examiner—Daniel S. Larkin
Assistant Examiner—Rose M. Miller
(74) Attorney, Agent, or Firm—Marks & Clerk

(57) ABSTRACT

A method and an apparatus for non-contact and non-invasive characterization of a moving thin sheet and in particular of a paper web on a production line. The method uses a laser for the generation of sonic and ultrasonic waves in the thin sheet and a speckle insensitive interferometric device for the detection of these waves. The generation is performed in conditions to avoid damage impeding further use of the sheet. When the generation and detection spots overlap, the method provides a measurement of the compression modulus. When the generation and detection spots are separated by a known distance and plate waves (Lamb waves) are generated and detected, the method provides a measurement of the in-plane modulus and of the tension applied to the sheet. By detecting waves propagating in various directions, either by rotating the detection sensor head or multiplexing the signals provided by several detection or generation locations, the anisotropy of the in-plane modulus is determined.

43 Claims, 7 Drawing Sheets

LASER-ULTRASONIC MEASUREMENT OF ELASTIC PROPERTIES OF A THIN SHEET AND OF TENSION APPLIED THEREON

CROSS REFERENCE TO RELATED APPLICATION

This application claims the benefit under 35 USC 119(e) of U.S. Provisional application Ser. No. 60/107,069 filed Nov. 4, 1998.

BACKGROUND OF THE INVENTION

Field of the Invention

This invention relates to the determination of the elastic properties of a thin sheet and to the measurement by laser-ultrasonics of the tension applied to a thin sheet. This invention is particularly useful for paper making and printing.

DESCRIPTION OF PRIOR ART

There is currently a great interest in industry to measure the elastic properties of thin sheets, either on the manufacturing line or off-line and to evaluate the tension applied to these thin sheets during processing. These measurements are particularly important for papermaking and printing as well as for aluminum foil rolling and plastic sheet fabrication. Regarding papermaking and printing, adequate tension applied to the web is fundamental for avoiding breaks and insuring optimum runnability. The in-plane elastic modulus of a paper web and its variation with direction are also important parameters to measure for evaluating the paper web quality. They are usually measured off-line with an apparatus that measures a parameter related to the in-plane modulus and called the tensile stiffness index (TSI). More precisely the TSI in a given direction is defined as the square of the acoustic velocity in this direction. The variation of the TSI with direction and the direction of its maximum value, called the Tensile Stiffness Orientation parameter (TSO), are also evaluated with this off-line apparatus. The paper web compressibility is also of interest, especially for printing, and can be estimated by through-thickness elastic modulus measurements.

Regarding the measurement of the tension applied on a thin sheet, the conventional method is to measure the load the sheet causes on a roller. Consequently, only the mean value over the sheet width is accessible and local tension peaks cannot be measured. To evaluate the variation of tension across a sheet, particularly across a paper web, sensors based on an applied force, sound waves or applied pressure have been designed. These sensors do not usually meet all the requirements of industry to measure the tension on a paper web running at high speed, as reviewed by H. Linna and P. Moilanen in *Comparison of methods for measuring web tension, Tappi Journal*, vol. 71, p. 134–138 (1988). They have prohibitive characteristics such as being slow, invasive, and sensitive to temperature changes. Although piezoelectric transducers have been developed for on-machine measurements, they have the drawback to be based on a contact approach. A non-contact method to measure the tension applied to a paper web was proposed by M. Luukkala and T. Marttinen in U.S. Pat. No. 4, 833, 928 entitled Method and apparatus for noncontacting tension measurement in a flat foil and especially in a paper web. The method is based on the generation of a sound wave by a piezoelectric transducer or a microphone and the detection of this sound wave by a laser-based triangulation technique. Although an improvement over other methods, the method proposed by M. Luukkala et al. suffers from the low sensitivity of laser-based triangulation techniques to acoustic motion.

Regarding the measurement of the elastic properties, various techniques for measuring the elastic properties of a static or moving paper web were recently reviewed in a publication by P. H. Brodeur, M. A. Johnson, Y. H. Berthelot, J. P. Gerhardstein, entitled *Noncontact laser generation and detection of Lamb waves in paper*, published in the Journal of Pulp and Paper Science, 23, J238, (1997). We summarize hereinbelow the main elements of this review. Contact methods based on a mechanical sensor for force measurement, ultrasonic transducers for Lamb wave generation and detection and friction-induced noise generator and microphone detection have been developed. As mentioned before, contact methods are not suitable for on-line measurement on a paper web moving at high speed. Two non-contact approaches have been investigated. The first method is based on air-coupled transducers to generate and detect ultrasonic and sonic waves propagating across the web. The reliability of this method is limited by the effect of ultrasonic absorption in air, sensitivity to moisture and air turbulence. The second method relies on lasers to generate and detect ultrasonic and sonic Lamb waves propagating across the web. Laser measurements of the ultrasonic and sonic surface motion of the paper web can be performed by laser-based triangulation methods and by interferometric methods, the later being much more sensitive. These laser methods have been described in various patents and publications and are discussed below.

The generation of acoustic waves has been reported to be performed by a Nd:YAG laser operated at its fundamental wavelength in the near infrared or at its second harmonic in the visible in U.S. Pat. No. 4,622,853 by M. A. Leugers entitled Laser induced acoustic generation for sonic modulus and in U.S. Pat. No. 5,814,730 by P. H. Brodeur, Y. H. Berthelot, J. P. Gerhardstein, M. A. Johnson entitled Material characteristic testing method apparatus using interferometry to detect ultrasonic signals in a web and also in the publication of B. Pouet, E. Lafond, B. Pufahl, D. Bacher, P. Brodeur, M. B. Klein entitled On-machine characterization of moving paper using a photo-electromotive force laser ultrasonic method published in Proceeding of SPIE, vol. 3589, p. 160, (1999). The use of an ultraviolet nitrogen laser was reported in U.S. Pat. No. 4,674,332 by S. A. Pace, S. S. Salama entitled Laser induced acoustic generation for sonic modulus. These two lasers, Nd-YAG and $N_2$ produce strongly fluctuating measurements from laser shot to laser shot and tend to induce damage on the paper web, as recognized by Y. H. Berthelot and M. A. Johnson in Laser ultrasonics in copy paper, Optical Engineering, vol. 36, pp. 408–416, (1997). In U.S. Pat. No. 5,025,665 entitled Non-contacting on-line paper strength measuring system, M. A. Keyes IV, W. L. Thompson considered the use of an infrared $CO_2$ laser (around a wavelength of 10 μm) with very long pulses, but this disclosure failed to indicate and discuss why this wavelength could be more appropriate for damage free generation of ultrasound in paper.

Regarding the detection of laser generated ultrasound, several methods were proposed in the patents and publications mentioned above. Detection can be performed by using a contact piezoelectric transducer or a microphone as proposed by M. A. Leugers in U.S. Pat. No. 4,622,853 and S. A. Pace, S. S. Salama in U.S. Pat. No. 4,674,332, or by using non-contact laser-based methods. As already mentioned, contact methods are not suitable for on-line measurements on a moving paper web. The non-contact methods proposed are either based on laser triangulation (M. A. Keyes IV, W.L. Thompson in U.S. Pat. No. 5,025,665), speckle sensitive interferometric heterodyne detection of the phase modulation produced by the ultrasonic motion of the paper web (P. H. Brodeur, Y. H. Berthelot, J. P. Gerhardstein, M. A. Johnson in U.S. Pat. No. 5,814,730) or a speckle insensitive photo-electromotive force based demodulator (B. Pouet et al, publication mentioned above). The heterodyne interferometric method used is sensitive to the speckle structure of the collected light, which results in a strongly fluctuating light level collected from the surface and a very large increase of the intensity noise seen by the optical detector. The speckle insensitive photo-electromotive force can be a basis of a laser-ultrasonic system for paper characterization, although the data reported with this device appears very noisy when the sheet is in rapid motion. Data is also only reported for the cross-machine direction. In the machine direction the Doppler effect produced by the sheet motion will decrease even more the signal-to-noise ratio.

In conclusion, all the previously described methods and techniques to either measure the tension or the mechanical properties of a sheet in motion (in particular a paper web) have drawbacks which limit their practical use. We have realized that laser-based generation and detection methods (called laser-ultrasonics) have the key advantage of being non-contact. We performed several experiments on static and moving paper sheets. For these experiments, a laser was selected that generated ultrasound in a reproducible manner without damaging the paper. The detection was performed using a confocal Fabry-Perot interferometer insensitive to the speckle structure of the collected light.

For most of the experiments, the samples were sheets of standard copy paper but other types of paper sheets were also tested positively. Tensions up to 1400 N/m were applied to the sheet of paper using calibrated weights. Data was analyzed by considering the sheet of paper as a vibrating membrane with stiffness. Assuming known the basis weight and the thickness of the paper sheet, an effective in-plane Young's modulus and the applied tension were determined. Measurements of the out-of-plane compression modulus were also reported.

In another set of experiments, the elastic properties of a paper web sheet were probed using the same basic setup. The in-plane sonic and ultrasonic displacement associated to the $S_o$ Lamb wave mode was detected using a detection laser impinging at an oblique incidence on the sheet. In-plane displacements induced by acoustic waves propagating in different directions were measured with a head mounted on a computer controlled rotation stage

SUMMARY OF THE INVENTION

According to the invention, there is provided a method for non-contact characterization of a sheet of material, preferably a sheet moving relative to the analyzing apparatus. The method involves the steps of irradiating the sheet with a beam of light at a first location to create an acoustic wave in the sheet; irradiating the sheet with a second different beam at a second location on the sheet; and demodulating the second beam to detect a signature of the acoustic wave within the second beam, the signature being characteristic of a property of the sheet. Further, according to the invention, there is provided an apparatus for non-contact and non-invasive characterization of a sheet, the sheet preferably moving relative to the apparatus, the apparatus comprising: a first means for illuminating a first location of the sheet with a first beam and for generating acoustic waves propagating through the sheet thickness and over its surface, a second means for illuminating a second location of the sheet with a second beam, on the same side or opposite side of the sheet, the second location being spaced from the first location by a predetermined distance, the sheet scattering the second beam to produce a scattered beam having a plurality of speckles, means for collecting the scattered beam, such collected beam having a phase and frequency modulation representative of the acoustic motion at this second location, and for demodulating the phase and frequency modulation to provide a signal representative of the acoustic motion at the second location, and analyzing means for analyzing the signal so as to determine a characteristic or a set of characteristics of the sheet.

BRIEF DESCRIPTION OF THE DRAWINGS

For a more complete understanding of the present invention and for further objects and advantages thereof, reference may be made to the following description taken in conjunction with the accompanying drawings in which.

DETAILED DESCRIPTION OF THE PREFERRED EMBODIMENTS OF THE INVENTION

Figure 1:
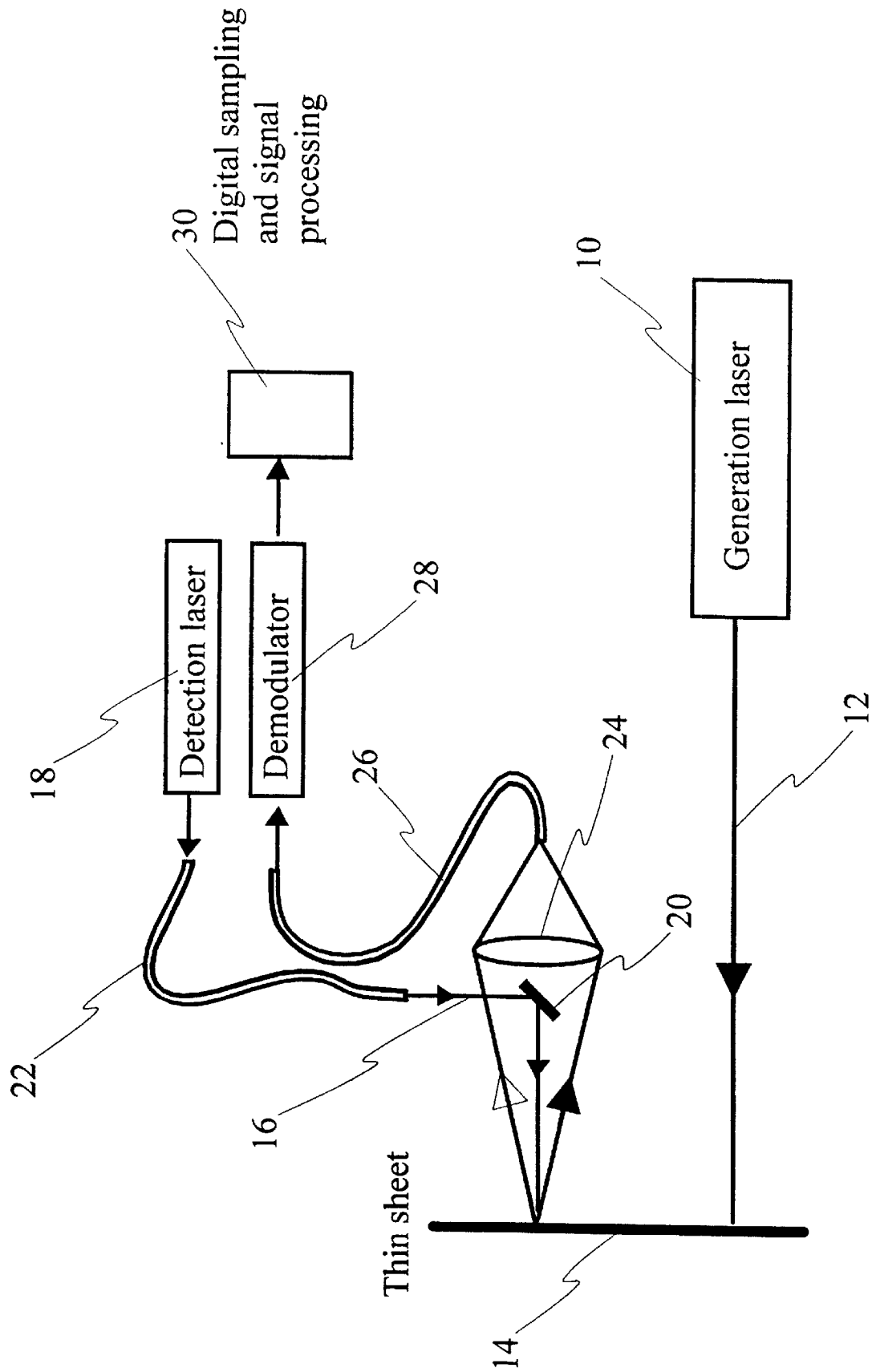
FIG. 1 is a schematic block diagram illustrating a sonic and ultrasonic generation and detection apparatus for measurement of the out-of-plane acoustic displacement of a thin sheet, wherein the detection laser is normal to the surface of the thin sheet and the collection of the light scattered or reflected by the thin sheet is also in a normal direction.

FIG. 1 shows a first embodiment according to the invention in which a beam 12 from a laser 10 is sent onto a moving thin sheet 14 and generates sonic and ultrasonic waves propagating throughout the sheet. This embodiment, as it will be explained below, is particularly appropriate for the measurement of the tension applied to the sheet. Generation is based on a thermoelastic mechanism: laser light is absorbed by the sheet, absorbed energy produces a transient heat source, which in turn, by thermal expansion, produces transient forces at the source of the launched acoustic waves. The types of waves launched are plate waves, essentially the anti-symmetric wave $A_o$ and the symmetric wave $S_o$, and a longitudinal bulk wave propagating through the thickness of the sheet. $A_o$ and $S_o$ are dispersive waves i.e. their velocities (phase or group velocities) are frequency dependent. At low frequencies $S_o$ is practically non-dispersive and is essentially an extensional wave having only in-plane displacement. $A_o$, is strongly dispersive at low frequencies and its velocity vanishes at zero frequency unless a tension is applied to the sheet. In this low frequency range, the antisymmetric wave becomes a non-dispersive membrane wave as described in the textbook *Theoretical Acoustics* (McGraw Hill, New-York) by P. M. Morse and K. U. Ingard and its phase velocity ($v_p$) is only determined by the applied tension T and the mass per unit area σ (called basis weight in the paper industry):

$$v_p = \sqrt{\frac{T}{\sigma}}$$

This formula is the basis of the tension determination, although a more elaborate analysis that takes into account membrane stiffness is needed in practice as explained below.

The generation laser used in our method is preferably selected such as to produce on the sheet no adverse mark that could impede subsequent use of the sheet. In the case of paper used for printing there should be no laser mark that appears after printing. We found that a TEA carbon dioxide laser operating around 10.6 μm is very appropriate for generation on paper without any damage. The energy density on the sheet has however to be limited to some threshold value. This value is lower for quality paper used for fine prints than for standard copy paper or newsprint paper. The carbon dioxide laser is also suitable for generation on polymer films. In both cases the performance of the TEA $CO_2$ laser is explained by its relatively long pulse (100 ns typically) and the progressive absorption of laser light below the surface, which produces a heat source and an acoustic source distributed below the surface and in turn, strong acoustic emission without damage. Much shorter pulse and high peak power lasers operating in the near infrared, such as the Nd-YAG, or in the visible or ultraviolet range tend to ablate the surface and are not generally suitable. Other lasers that operate at a wavelength absorbed by the material could also be suitable. For paper, we note in particular the Erbium-YAG laser operating around 2.9 μm, a wavelength that is absorbed by the OH-stretch band of cellulose fibers. In the case of metal sheets, non-invasive strong generation is more difficult with any laser and the laser power density has to be drastically limited to avoid any damage, so generation stays within the thermoelastic regime.

The generation laser is shown in FIG. 1 to be directly coupled to the sheet. It could also be coupled through an optical fiber. Present technological limitations will make this fiber rather short in case of the TEA $CO_2$ (typically one meter). Much longer lengths (several tens of meters) are readily feasible with shorter wavelength lasers such as the Erbium-YAG, thus making it possible to have the laser located far away of the production line.

As shown in FIG. 1, a beam 16 from a second laser 18 is used for detection of the acoustic motion of the sheet 14 and it impinges on the sheet at normal incidence after reflection by a mirror 20. In FIG. 1, this laser beam 16 is shown to be transmitted by an optical fiber 22, which is usually readily feasible since this laser is usually in the visible or near-infrared range (such as the Nd-YAG laser operating at 1.06 μm). The laser beam can also be directly coupled. The two laser beams 12, 16 impinge on the moving sheet 14 at different locations separated by a known distance. The two laser beams are shown to illuminate the sheet from the same side, but since the acoustic wave generated and detected is a plate or Lamb wave and involves motion of the whole sheet, the two beams could be as well on opposite sides of the sheet. The light from the detection laser scattered off the thin sheet is then collected by a lens 24 and transmitted by an optical fiber 26 to a large étendue (throughput) speckle insensitive interferometric demodulator 28. The demodulator includes an optical detector (not illustrated) that provides an electrical signal representative of the acoustic motion of the sheet. This signal is then digitized and processed by a digital sampling and processing unit 30. The demodulator could be a confocal Fabry-Perot interferometer used in transmission or reflection (for a very thin sheet) as described in U.S. Pat. Nos. 4,659,224 and 4,966,459 (J.-P. Monchalin) and U.S. Pat. No. 5,137,361 (R. Héon and J.-P. Monchalin). Alternatively, a two-wave mixing scheme in a photorefractive crystal could be used as described in U.S. Pat. No. 5,131,748 by J.-P. Monchalin and R. K. Ing and U.S. Pat. No. 5,680,212 by A. Blouin, P. Delaye, D. Drolet, J.-P. Monchalin and G. Roosen. The Fabry-Perot scheme is usually preferred whenever the sheet is rough and is in rapid motion, such as a paper web, or is affected by large vibrations, since this scheme has a more rapid response for adaptation to a change of the speckle pattern and is more tolerant to change of the frequency of the scattered light caused by a vibrating motion of the sheet (Doppler effect). It also possible to use, although usually with a lesser sensitivity, a very simple demodulator based on the photo-electromotive force effect, as described by M. P. Petrov, I. A. Sokolov, S. I. Stepanov, G. S. Trofimov, in Journal of Applied Physics, vol. 68, p 2216, 1990 entitled *Non-steady-state photo-electromotive-force induced by dynamic gratings in partially compensated photoconductors*. It should be noted that it is very important in the case of a sheet like paper to use a speckle insensitive large étendue interferometer. The large number of speckles collected in this case minimizes the noise introduced by the sheet motion. In the case of a speckle sensitive interferometer, as used by Brodeur et al. (U.S. Pat. No. 5,814,730) this noise would have been extremely large, as mentioned previously.

Figure 7:
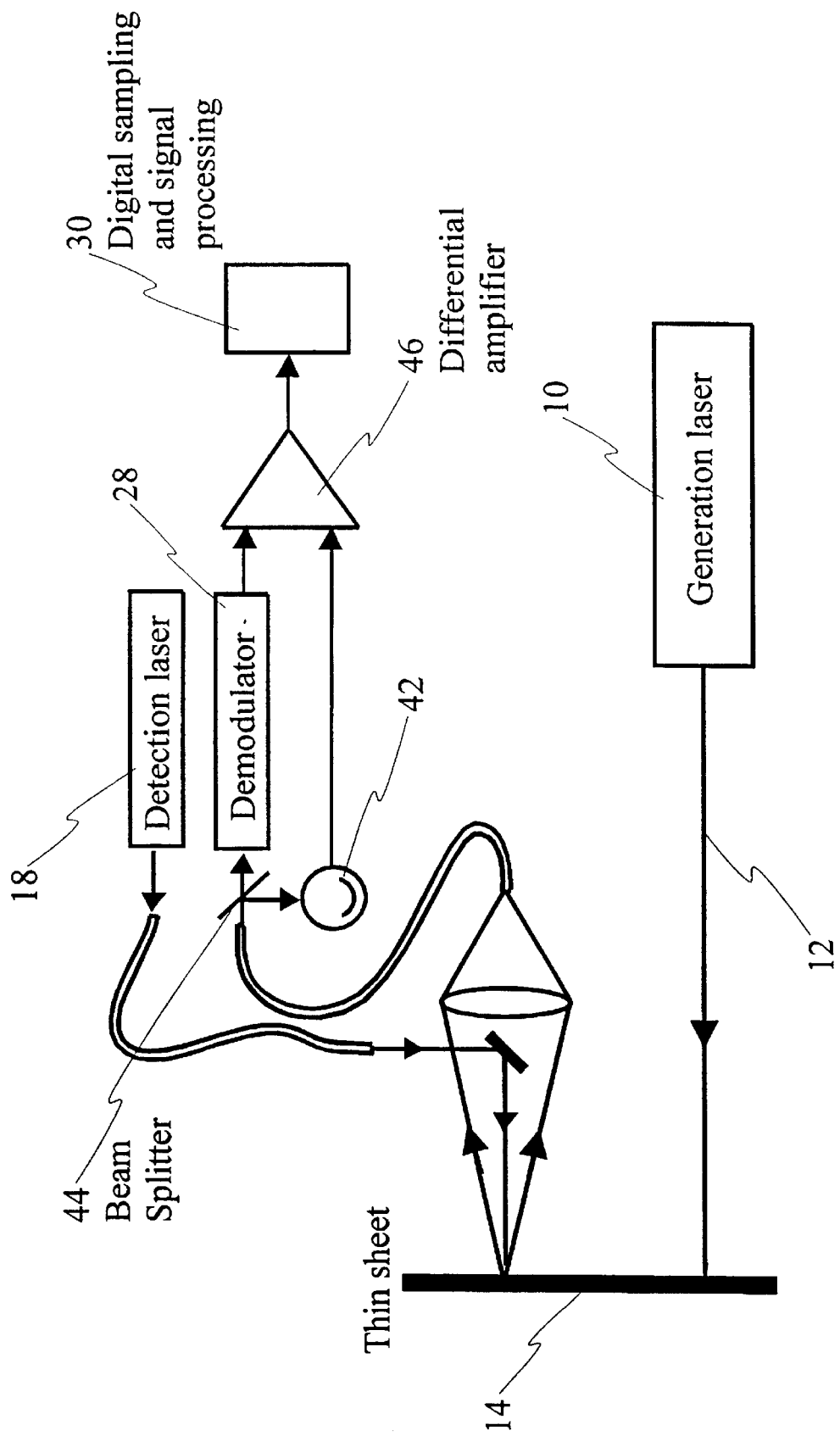
FIG. 7 is a schematic diagram of an embodiment of the apparatus of the invention with a noise correction unit.

Furthermore we found that in the case of paper, the noise that appears at the output of the demodulator for a paper sheet in motion is essentially intensity noise and consequently could be subtracted from the signal at the output of the demodulator. To perform this correction a detector 42 (FIG. 7) with the same detection bandwidth as the one of the demodulator is set ahead of the demodulator 28 and picks up through a beam splitter 44 a fraction of the light sent onto the demodulator. The signal from this additional detector is then subtracted from the signal of the demodulator with a differential amplifier 46 to provide an electrical signal substantially free of the intensity fluctuations caused by the sheet motion. This is strictly valid at sufficiently low frequencies for which the frequency response to amplitude modulation of the demodulator (especially confocal Fabry-Perot) is essentially flat, otherwise one should take into account this response. Alternatively one could use a demodulator insensitive to intensity fluctuations such a demodulator with a differential detection scheme, as described in U.S. Pat. No. 5,080,491 by J.-P. Monchalin and R. Héon for the Fabry-Perot or a two-wave mixing scheme (see U.S. Pat. Nos. 5,131,748 and 5,680,212 mentioned above) or a photo electromotive force scheme. An alternative to this compensation scheme, which also diminishes the noise of any origin, is to average signals obtained at various times during sheet motion. Averaging could also be used in addition to the compensation scheme to improve further the signal-to-noise ratio.

Figure 2:
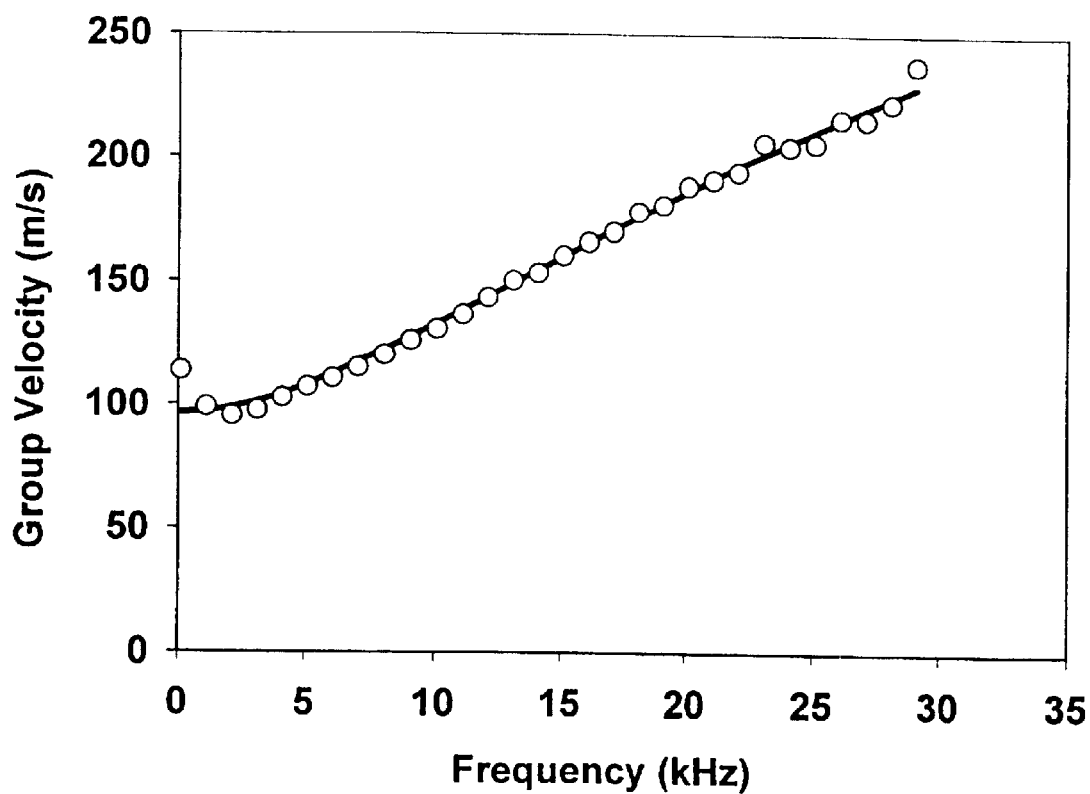
FIG. 2 shows a plot of the group velocity dispersion obtained experimentally on a sheet of paper and the theoretical fit.

In the embodiment of FIG. 1, the normal incidence of the detection beam and the normal collection of the scattered laser light allow to detect only the out-of-plane sonic and ultrasonic displacements produced by the generation laser. Alternatively the direction of incidence of the detection beam and the direction of light collection could be symmetric with respect to the normal of the sheet and only out-of-plane displacements would be detected. This out-of-plane displacement is related to the $A_o$ Lamb wave mode of the sheet. Since the distance between the generation and detection spots is known the phase and group velocities of the $A_o$ mode can be obtained from the time delay between generation and detection of the displacement. The phase velocity $v_p$ of the $A_o$ ultrasonic wave propagating on a membrane can be found in the publication by S. W. Wenzel and R. W. White, *A Multisensor Employing an Ultrasonic Lamb-Wave Oscillator*, IEEE Journal of Quantum Electronics, vol. 35, p. 735, (1988) and is given by:

$$v_p = \sqrt{\frac{T}{2\sigma} + \sqrt{\left(\frac{T}{2\sigma}\right)^2 + \frac{\pi^2 f^2 d^3 Y_f}{3\sigma}}} \quad \text{with} \quad Y_f = \frac{Y}{1-v^2}$$

were d is the thickness of the thin sheet, f is the frequency of the ultrasonic wave, T is the applied tension, $\sigma$ is the basis weight, Y is the in-plane Young's modulus (a measure of the stiffness of the sheet) and v is the Poisson ratio. Experimentally, we can obtain the phase velocity by measuring the phase delay of the acoustic waves propagating over a known distance. This usually requires to measure the signal at two different detection points since the initial phase, at the generation point, is unknown. Alternatively, the measurement of the group velocity $v_g$ necessitates only one detection point, since it is insensitive to the initial phase. Hence, knowing the propagation distance between the generation and the detection points, the group velocity can be determined. More precisely, the dispersion of the ultrasonic group velocity can be extracted from the laser-ultrasonic data using the method described by J.-D. Aussel in U.S. Pat. No. 5,035,144 entitled Frequency broadband measurement of the characteristics of acoustic waves. From the relation between the phase and the group velocities given below:

$$v_g = \frac{v_p^2}{v_p - f\frac{dv_p}{df}}.$$

and the previous equation, we obtain readily the equation giving the group velocity as a function of tension, of the effective Young's modulus $Y_f$, of the basis weight and the thickness. Assuming the basis weight and the thickness of the sheet known, the value of the effective Young's modulus $Y_f$ and of the tension applied to the sheet are then obtained from a fit of the equation giving the group velocity to the experimental data. Note that the tension is essentially determined by the asymptotic low frequency value. An example of such a fit to experimental data is shown in FIG. 2 for a sheet of standard copy paper.

In the case of a null distance between generation and detection spots, which means superimposed spots, through thickness echoes are observed. From the measurements of the time-of-flight, the through-thickness velocity ($v_L$) is determined, assuming known the thickness d. Assuming further known the basis weight $\sigma$, the compression modulus or elastic constant $C_{11}$ is then determined by the well known equation:

$$C_{11} = \frac{V_L^2 \sigma}{d}$$

the symbols being as explained above.

Figure 3:
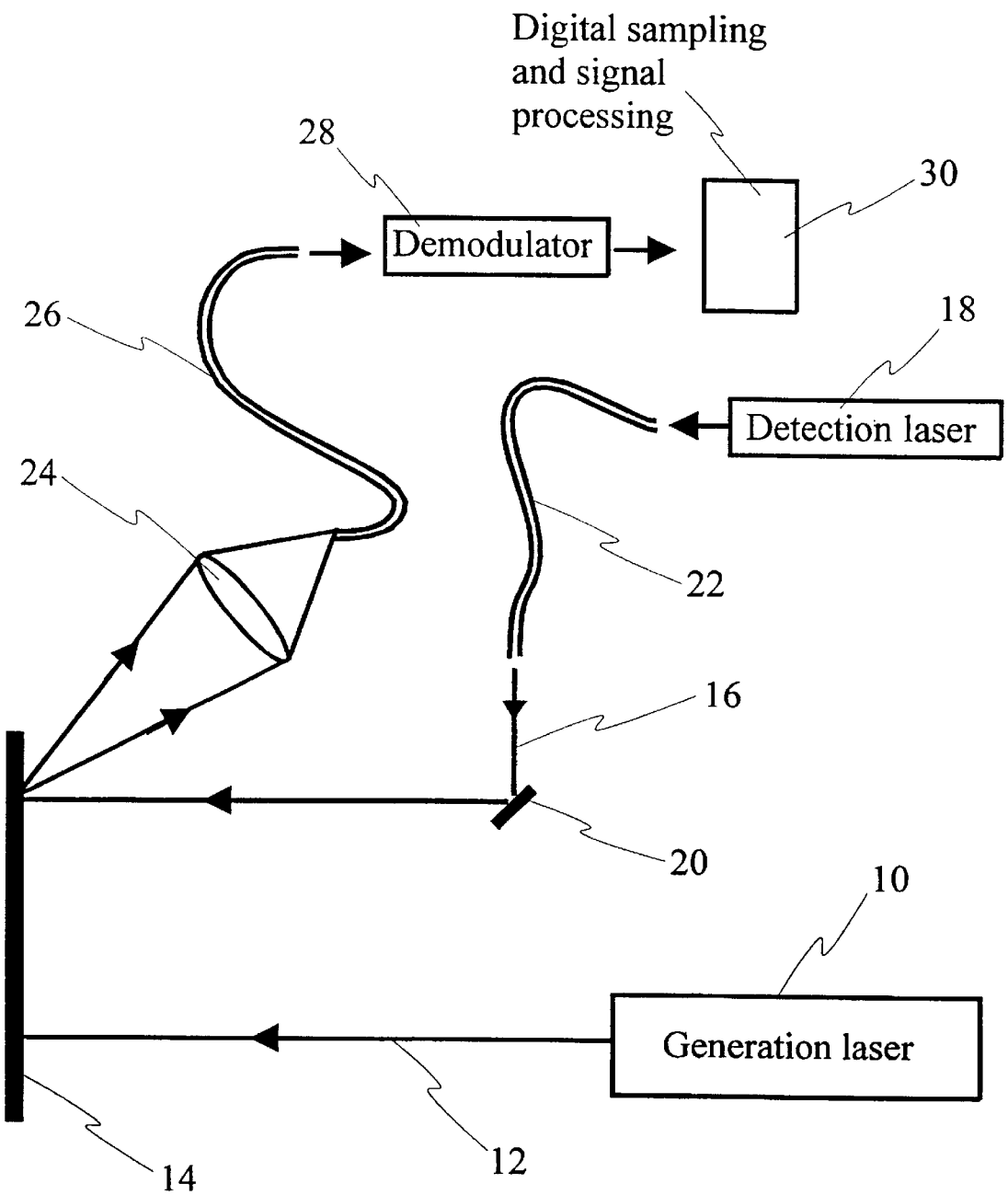
FIG. 3 is a schematic block diagram illustrating a sonic and ultrasonic generation and detection apparatus for the measurement of the out-of-plane and in-plane acoustic displacements of a thin sheet, wherein the detection laser is normal to the surface of the thin sheet and the light scattered by the sheet is collected along an oblique direction.

In a second embodiment shown in FIG. 3, the light scattered off the thin sheet is collected at an oblique incidence. In this embodiment, both the out-of-plane and the in-plane sonic and ultrasonic displacements are measured. The in-plane ultrasonic and sonic displacements are related to the $S_o$ Lamb wave mode of the sheet. Since the distance between the generation and detection spots is known the phase and group velocities of the $S_o$ mode can be obtained from the time delay between generation and detection. The in-plane stiffness or Young modulus of the sheet can be derived from these measurements. More precisely, in the case of paper, the tensile stiffness index (TSI) in a given direction (defined as the square of the acoustic velocity in this direction) is obtained from these measurements. Note that it is possible to detect simultaneously the two waves $A_o$ and $S_o$ waves because they have very different velocities and $S_o$ actually arrives much earlier than $A_o$.

Alternatively instead of having the illuminating beam for detection normal to the sheet and detection at an angle, the detection direction could be normal and the illuminating beam can be directed at an angle.

Figure 4:
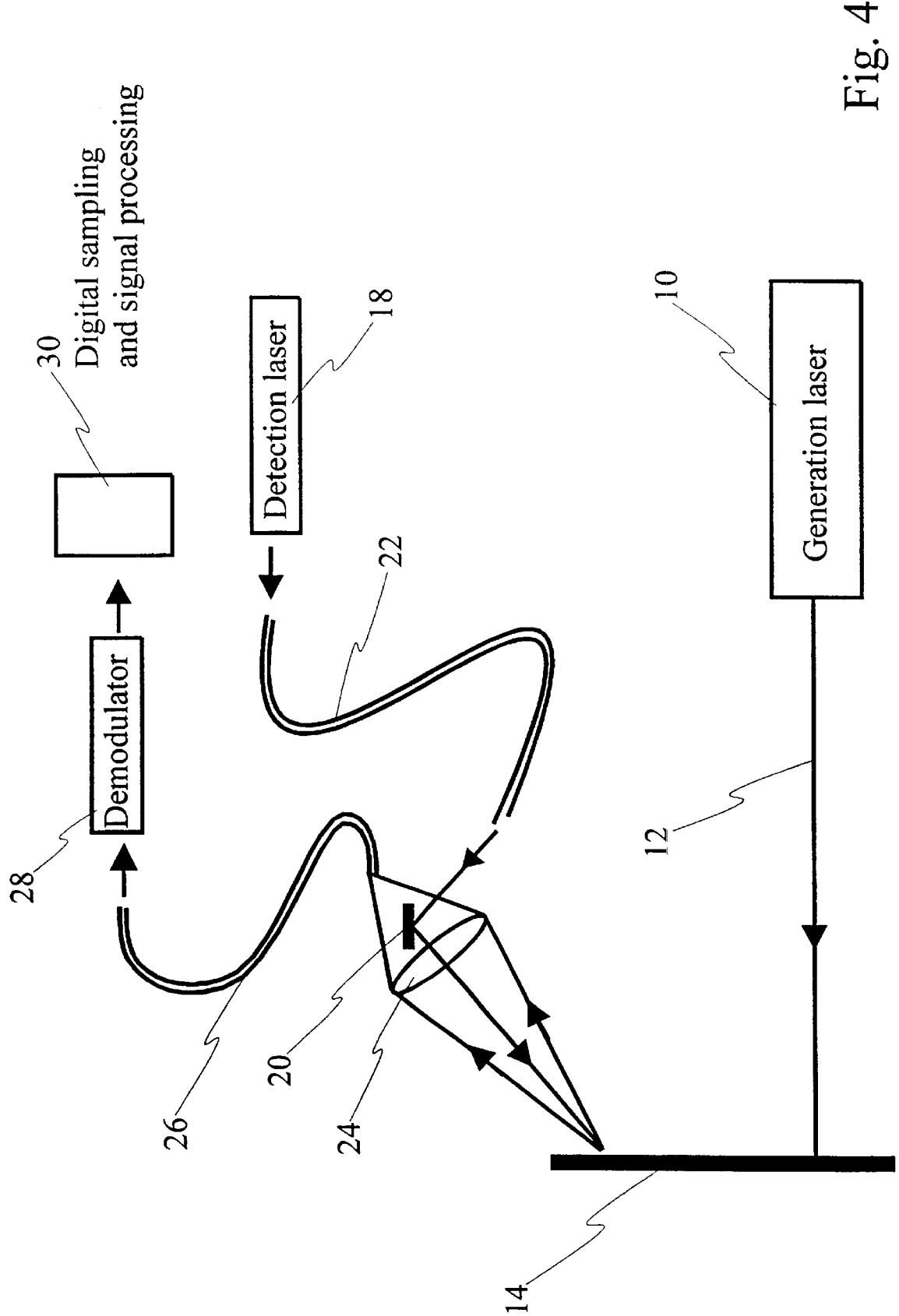
FIG. 4 is a schematic block diagram illustrating a sonic and ultrasonic generation and detection apparatus for the measurement of the out-of-plane and in-plane acoustic displacements of a thin sheet, wherein the detection laser is oblique to the surface of the thin sheet and the light scattered by the thin sheet is collected along the same direction as the detection laser.

In a third embodiment shown in FIG. 4, the detection laser impinges on the sheet at an oblique incidence and the light scattered off the thin sheet is collected along the same oblique incidence. In this embodiment, both the out-of-plane and the in-plane sonic and ultrasonic displacements are also measured. In this embodiment the sensitivity to in-plane displacement is doubled compared to the embodiment of FIG. 3.

Figure 5:
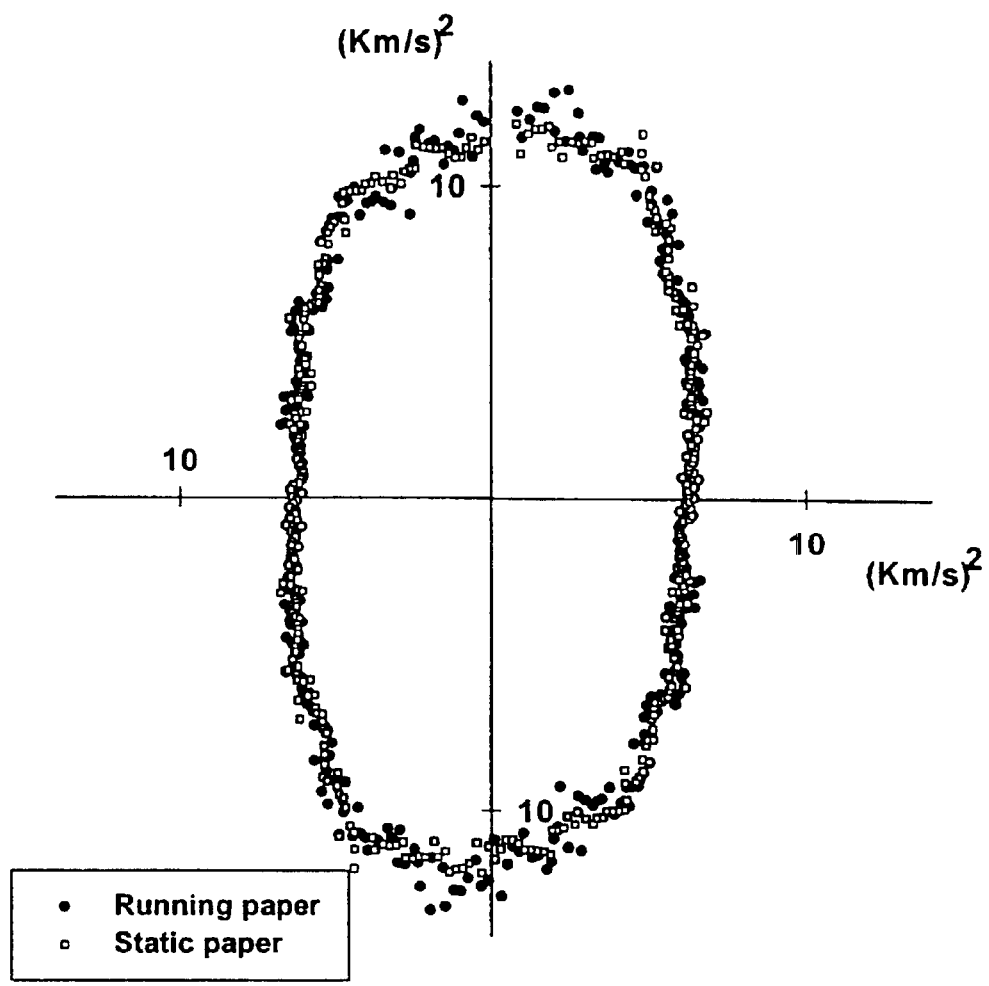
FIG. 5 shows the polar plots of the Tensile Stiffness Index (TSI) of a sheet of paper measured in static and dynamic conditions (paper velocity 11 m/s)

Since it is of interest to measure the modulus and the tension in various directions, the detection assembly shown in FIGS. 3 and 4 can be mounted on a computer controlled rotation stage to allow the measurements of these parameters as a function of direction. In particular, in the case of paper, the variation of the TSI with direction and the direction of its maximum value, called the Tensile Stiffness Orientation parameter (TSO), can be determined in this way. An example of data obtained with this technique on a paper sheet is shown in FIG. 5. FIG. 5 actually plots the TSI as a function of direction for the sheet stationary and for the sheet in motion at a velocity of 11 m/s. For this data, a TEA $CO_2$ laser was used for generation and a confocal Fabry-Perot for detection. This data demonstrates the capability of our technique to measure the TSI of a paper sheet in rapid motion and it should be noted that these results were obtained without any damage to the sheet.

Figure 6:
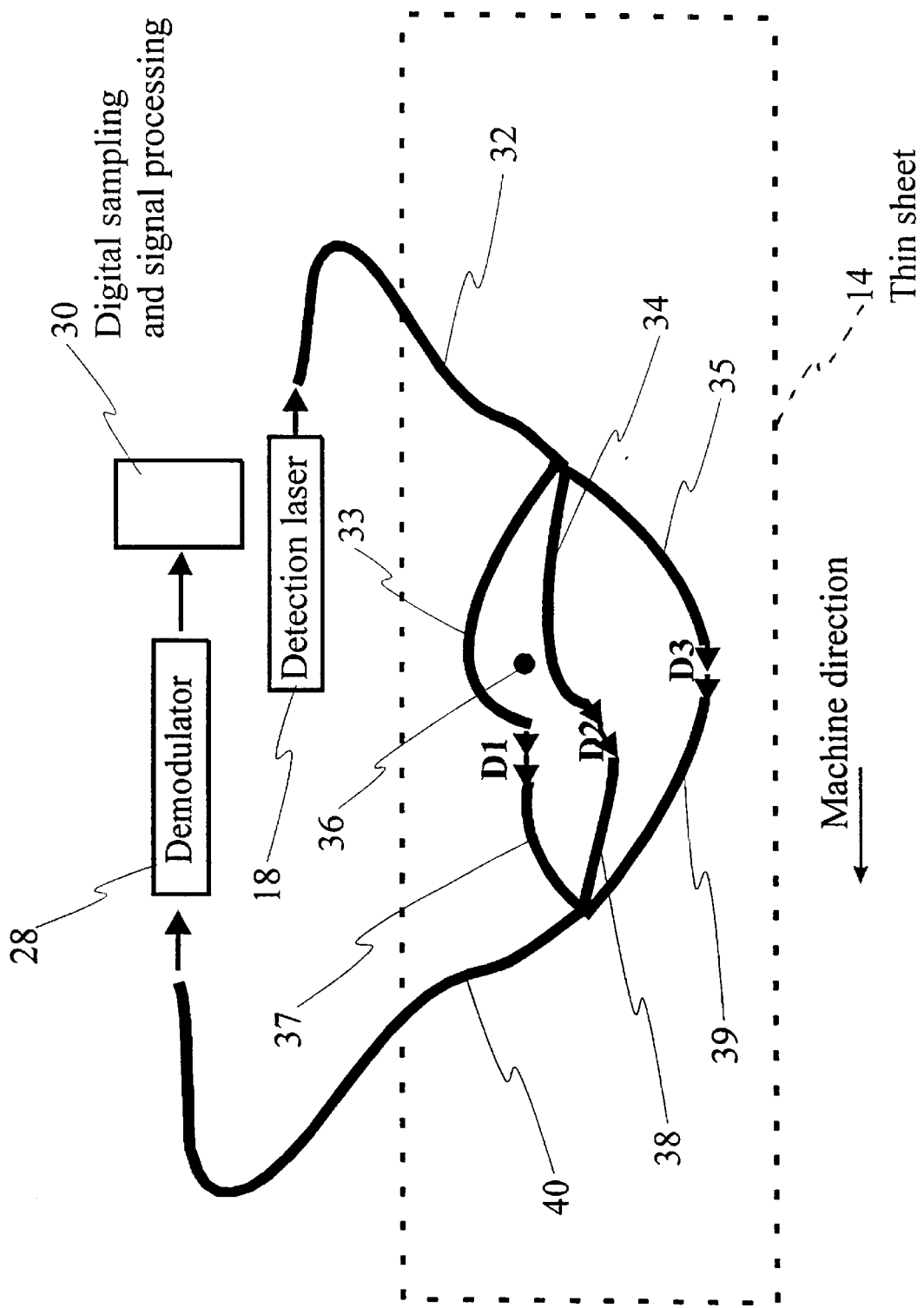
FIG. 6 is a schematic block diagram illustrating a multiple detection head apparatus for the detection of the out-of-plane and in-plane acoustic displacements of a thin sheet.

This determination can also be performed without a rotating part by an optical multiplexing scheme as shown in FIG. 6. The detection laser 18 is coupled through a large core multimode fiber 32 which is then split into three fibers 33, 34, 35 to give three beams that impinge on the sheet at locations $D_1$, $D_2$ and $D_3$. Scattered light is then collected by three large core multimode fibers 37, 38, 39 that are fused into a single fiber 40, which finally couples the received light onto the demodulator 28. The illumination and the detection directions are properly tilted to detect both $A_o$ and $S_o$ waves.

The locations of $D_1$, $D_2$ and $D_3$ with respect to the generation spot 36 are such that one detects the acoustic wave traveling in the machine direction (with $D_1$), the wave traveling at 45° to the machine direction (with $D_2$) and the wave traveling at 90° in the cross-machine direction (with $D_3$). These three detection spots are also located at different distances from the generation spot 36 to introduce a time delay between the arrivals of the acoustic waves from different directions. Hence, as shown in FIG. 6, a single detection channel can be used and the signal associated to a given direction is well separated from the others in the output signal. This three-channel configuration allows therefore measurement of the anisotropy of the in-plane stiffness without any rotating part. This multiplexing method was illustrated in FIG. 3 by showing three different locations, but obviously more locations could be used so as to improve the resolution and accuracy of the determination of the anisotropy of the in-plane stiffness. Alternatively, the generation laser beam 12 can be separated in several beams that impinge on the sheet at different locations. These generation locations define with the single detection spot different directions of measurement. The generation spots are also located at different distances from the detection spot, so as to introduce time delays to separate the contributions from the various directions. Another alternative, while using a single generation location and several detection spots, is to use an array of demodulators of large étendue, as described in the U.S. Pat. No. 5,402,235, Imaging of ultrasonic-surface motion by optical multiplexing by J.-P. Monchalin. In this case the three (or more) collection fibers shown in FIG. 6 would not be fused together but will transmit their light signals to distinct elements of the array.

Finally it is noted that, except when measuring in the cross-machine direction (perpendicular or transverse to the direction of motion of the sheet), a correction is made on the measured acoustic velocity to take into account the velocity of the sheet itself, which is always known with sufficient accuracy. This correction is nearly negligible for the $S_o$ wave but is significant for $A_o$.

What is claimed is:

1. A method for non-contact characterization of a rapidly moving sheet, comprising the steps of:
    illuminating the sheet at a first location with a first pulsed laser beam for generating acoustic waves propagating through the sheet thickness and over its surface,
    illuminating the sheet at a second location with a second laser beam, on the same side or the opposite side of the sheet, this second location being spaced from the first location by a predetermined distance, said sheet scattering the second beam to produce a scattered beam with a plurality of speckles,
    collecting the scattered beam, such collected scattered beam having a phase or frequency modulation representative of the acoustic motion at the second location, and
    demodulating the phase or frequency modulation to provide an electrical signal representative of the acoustic motion at the second location, and
    analyzing the electrical signal to determine a characteristic or a set of characteristics of the sheet,
    characterized in that said first laser has a wavelength selected to ensure progressive absorption below the surface of the sheet so as to produce a distributed acoustic source below the surface and an intensity below a threshold value to avoid damage to the sheet, and said demodulating of the phase or frequency modulation is carried out with a speckle-insensitive interferometer.

2. A method as described in claim 1 wherein the sheet is a paper web.

3. A method as described in claim 2 whereby the sheet is a paper web used for printing.

4. A method as described in claim 1 whereby the sheet is of a polymer.

5. A method as described in claim 1 whereby the sheet is of metal.

6. A method as described in claim 1 whereby the characteristic is the tension applied to the sheet.

7. A method as described in claim 1 whereby the characteristic is an elastic modulus.

8. A method as described in claim 1 whereby the set of characteristics consists in the variation of the in-plane elastic modulus in various directions.

9. A method as described in claim 1 and applied to a paper web whereby, the set of characteristics is the Tensile Stiffness Index in various directions of the paper web.

10. A method as described in claim 1 including further the averaging of signals obtained at various times during sheet motion to further minimize additional noise introduced by sheet motion.

11. A method as described in claim 1 whereby additional noise introduced by sheet motion is substantially diminished by subtracting a signal representative of the fluctuations of intensity of the collected light prior to demodulation.

12. A method as described in claim 1 whereby second laser beam is sent substantially perpendicular to the sheet surface and scattered light is collected in a direction also substantially perpendicular to the sheet surface or second laser beam and collection direction are at an angle and are substantially symmetric with respect to the normal to the sheet surface to detect through thickness ultrasonic motion or out-of-plane motion associated to the AO Lamb acoustic wave.

13. A method as described in claim 1 whereby the second laser beam is directed substantially perpendicular to the sheet surface and the scattered beam is collected at an angle or the other way around or both are substantially in the same direction at an angle with respect to the normal to the sheet to detect in-plane acoustic motion associated to SO Lamb ultrasonic wave.

14. A method as described in claim 1 whereby second laser beam is sent substantially perpendicular to the sheet surface and scattered light is collected at an angle or the other way around or both are substantially in the same direction at an angle with respect to the normal to the sheet to detect both out-of-plane and in-plane acoustic motion.

15. A method as described in claim 1 whereby the step of signal analyzing consists of deriving the tension applied to the sheet from the asymptotic low frequency value of the phase or group velocity dispersion curve calculated from the out-of-plane displacement signal associated to the AO Lamb wave mode.

16. A method as described in claim 1 whereby the step of signal analyzing consists of deriving the in-plane modulus from the velocity calculated from the in-plane displacement signal associated to the SO Lamb wave mode.

17. A method as described in claim 1 whereby the second location overlaps the first location and whereby signal analysis consists in deducing from the through-thickness echoes the through-thickness velocity and from the through-thickness velocity the compression modulus or compressibility.

18. A method as described in claim 1 whereby several detection locations are used to measure simultaneously the velocity of SO and AO modes in various directions and to obtain the angular distribution of tension and tensile modulus.

19. A method as described in claim 1 whereby several generation locations are used to measure simultaneously the velocity of SO and AO modes in various directions and to obtain the angular distribution of tension and tensile modulus.

20. An apparatus for non-contact and non-invasive characterization of a rapidly moving sheet, comprising:
a first means for illuminating a first location of the sheet with a first laser beam and for generating acoustic waves propagating through the sheet thickness and over its surface,
a second means for illuminating a second location of the sheet with a second laser beam, on the same side or the opposite side, the second location being spaced from the first location by a predetermined distance,
a third means for collecting the scattered beam, such collected light having a phase or frequency modulation representative of the acoustic motion at this second location,
means for demodulating the phase or frequency modulation so as to provide an electrical signal representative of the acoustic motion at this second location, and
analyzing means for analyzing the electrical signal so as to determine a characteristic or a set of characteristics of the rapidly moving sheet,
characterized in that said first means has a wavelength selected to ensure progressive absorption below the surface of the sheet so as to produce a distributed acoustic source below the surface and an intensity below a threshold value to avoid damage to the sheetd, and said demodulating means comprises speckle-insensitive interferometer.

21. An apparatus as described in claim 20 whereby the sheet is a rapidly moving paper web.

22. An apparatus as described in claim 21 whereby the sheet is a paper web used for printing.

23. An apparatus as described in claim 20 whereby the sheet is of a polymer.

24. An apparatus as described in claim 20 whereby the sheet is of a metal.

25. An apparatus as described in claim 20 whereby the characteristic is the tension applied to the sheet.

26. An apparatus as described in claim 20 whereby the characteristic is an elastic modulus.

27. An apparatus as described in claim 20 whereby the set of characteristics consists in the variation of the in-plane elastic modulus in various directions.

28. An apparatus as described in claim 20 and used on a paper web whereby the set of characteristics is the Tensile Stiffness Index in various directions of the paper web.

29. An apparatus as described in claim 20 further including averaging means acting on the signals obtained at various times during sheet motion and used prior to analysis to further minimize additional noise introduced by sheet motion.

30. An apparatus as described in claim 20, including further detector means to measure the fluctuations of intensity ahead of interferometric means and subtraction means to subtract detector means signal from said electrical signal to minimize additional noise introduced by sheet motion.

31. An apparatus as described in claim 20 whereby second means sends second laser beam substantially perpendicular to the sheet surface and third means collects scattered light in a direction also substantially perpendicular to the sheet surface or second means sends laser beam at an angle and third means collects scattered light in a direction substantially symmetric with respect to the normal to the sheet surface to detect through thickness ultrasonic motion or out-of-plane motion associated to the AO Lamb acoustic wave.

32. An apparatus as described in claim 20 whereby second means sends second laser beam in a direction making an angle with respect to the sheet surface and third means collects scattered light in a direction substantially normal to the sheet surface or the other way around or both means have directions substantially the same and making an angle with respect to the sheet surface to detect in-plane acoustic motion associated to SO Lamb acoustic wave.

33. An apparatus as described in claim 20 whereby second means sends second laser beam in a direction making an angle with respect to the sheet surface and third means collects scattered light in a direction substantially normal to the sheet surface or the other way around or both means have directions substantially the same and making an angle with respect to the sheet surface to detect both out-of-plane and in-plane acoustic motion.

34. An apparatus as described in claim 20 whereby the analyzing means derives the tension applied to the sheet from the asymptotic low frequency value of the phase or group velocity dispersion curve calculated from the out-of-plane displacement signal associated to the AO Lamb wave mode.

35. An apparatus as described in claim 20 whereby the signal analysis means derives the in-plane modulus from the velocity calculated from the in-plane displacement signal associated to the SO Lamb wave mode.

36. An apparatus as described in claim 20 whereby the second location overlaps the first location and whereby the analyzing means first derives the through-thickness velocity from the through-thickness echoes and hence the compression modulus or compressibility from the through-thickness velocity.

37. An apparatus as described in claim 20 further including means for providing several detection locations to measure simultaneously the velocity of SO and AO modes in various directions and to obtain the angular distribution of tension and tensile modulus.

38. An apparatus as described in claim 20 further including means for providing several generation locations to measure simultaneously the velocity of $S_o$ and $A_o$ modes in various directions and to obtain the angular distribution of tension and tensile modulus.

39. An apparatus as described in claim 20 whereby the first means is a transversely excited atmospheric pressure carbon dioxide laser.

40. An apparatus as described in claim 20 whereby first means has a wavelength suitable to be absorbed by an OH band of the sheet material.

41. An apparatus as described in claim 20 whereby the speckle-insensitive interferometer is a confocal Fabry-Perot interferometer.

42. An apparatus as described in claim 20 whereby speckle-insensitive interferometer is based on two-wave mixing in a non-linear optical material.

43. An apparatus as described in claim 20 whereby the interferometric means is based on the photoelectromotive force effect in an optical material.

* * * * *